United States Patent [19]

Bailey et al.

[11] Patent Number: 5,053,500
[45] Date of Patent: Oct. 1, 1991

[54] INTERMEDIATES FOR THE PREPARATION OF BETA-LACTAM ANTIBIOTICS

[75] Inventors: John P. Bailey, Macclesfield, England; Georges Pasquet, Bazancourt, France

[73] Assignee: Imperial Chemical Industries PLC, London, England

[21] Appl. No.: 555,355

[22] Filed: Jul. 20, 1990

Related U.S. Application Data

[63] Continuation of Ser. No. 928,456, Nov. 10, 1986, abandoned.

[30] Foreign Application Priority Data

Nov. 21, 1985 [FR] France .............................. 85 402266

[51] Int. Cl.$^5$ .............................................. C07D 501/18
[52] U.S. Cl. ...................................... 540/215; 540/221
[58] Field of Search ............................................ 540/215

[56] References Cited

U.S. PATENT DOCUMENTS

| | | | |
|---|---|---|---|
| 3,539,562 | 11/1970 | Diassi et al. .......................... | 260/243 |
| 3,644,347 | 2/1972 | Webber et al. ....................... | 540/215 |
| 4,278,793 | 7/1981 | Dürckheimer et al. ............ | 424/246 |
| 4,347,358 | 8/1982 | Bruynes ................................ | 540/215 |
| 4,386,089 | 5/1983 | Konig et al. ......................... | 424/246 |
| 4,457,929 | 7/1984 | Kamachi et al. .................... | 424/246 |
| 4,614,819 | 9/1986 | Nagai et al. ......................... | 540/222 |

FOREIGN PATENT DOCUMENTS

| | | |
|---|---|---|
| 0224385 | 6/1987 | European Pat. Off. . |
| 2103205A | 2/1983 | United Kingdom . |

OTHER PUBLICATIONS

Chemical Abstracts vol. 107 236361x.

Primary Examiner—Nicholas S. Rizzo
Attorney, Agent, or Firm—Cushman, Darby & Cushman

[57] ABSTRACT

Cephalosporin derivatives of the formulae

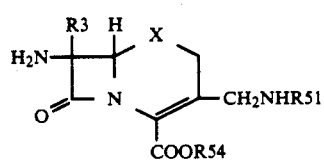

LIII

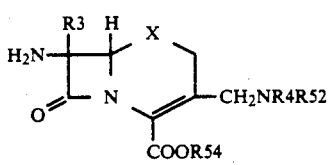

LIV wherein X is sulphur, oxygen, methylene or sulphinyl, R3 is hydrogen or methoxy, R54 is hydrogen or a carboxyl protecting group, $R^{51}$ is a (1-4C)alkyl group, $R^4$ is hydrogen, (1-4C)alkyl, halo(1-4C)alkyl, hydroxy(1-4C)alkyl, (1-4C)alkoxy(1-4C)alkyl, carboxy (1-4C)alkyl, amino (1-4C)alkyl, cyano(1-4C)alkyl, (1-4C)alkanoylamino(1-4C)alkyl, allyl, furfuryl, benzyl or pyridyl(1-4C)alkyl and $R^{52}$ is an amino protecting group and salts thereof are useful as intermediates in the preparation of cephalosporin antibiotics.

5 Claims, No Drawings

INTERMEDIATES FOR THE PREPARATION OF BETA-LACTAM ANTIBIOTICS

This is a continuation of application Ser. No. 06/928,456, filed on Nov. 10, 1986, which was abandoned upon the filing hereof.

The invention relates to intermediates for use in the preparation of cephalosporin derivatives.

In this specification formulae denoted by roman numerals are set out on separate sheets.

Our copending European Patent Application No. 85303662.2 (published No. 164944) describes cephalosporin derivatives of the formula I in which X is sulphur, oxygen, methylene or sulphinyl (R or S configuration);

R1 is 2-aminothiazol-4-yl or 2-aminoooxazol-4-yl each optionally substituted in the 5-position by fluorine, chlorine or bromine, or R1 is 5-aminoisothiazol-3-yl, 5-amino-1,2,4-thiadiazol-3-yl, 3-aminopyrazol-5-yl, 3-aminopyrazol-4-yl, 2-amino-pyrimidin-5-yl, 2-aminopyrid-6-yl, 4-aminopyrimidin-2-yl, 2-amino-1,3,4-thiadiazol-5-yl or 5-amino-1-methyl-1,2,4-triazol-3-yl;

R50 is chloromethylene or a radical of the formula =N.O.R2, wherein R2 is hydrogen, (1–6C)alkyl, (3–8C)cyclo-alkyl, (1–3C)alkyl(3–6C)cycloalkyl, (3–6C)cycloalkyl(1–3C)alkyl, (3–6C)alkenyl, optionally substituted by carboxy, (5–8C)cycloalkenyl, (3–6C)alkynyl, (2–5C)alkylcarbamoyl, phenylcarbamoyl, benzylcarbamoyl, (1–4C)alkylcarbamoyl(1–4C)alkyl, di(1–4C)alkylcarbamoyl(1–4C)alkyl, (1–4C)haloalkylcarbamoyl(1–4C)alkyl, triphenylmethyl, (1–3C)haloalkyl, (2–6C)hydroxyalkyl, (1–4C)alkoxy(2–4C)alkyl, (1–4C)alkylthio(2–4C)alkyl, (1–4C)alkanesulphinyl(1–4C)alkyl, (1–4C)alkanesulphonyl(1–4C)alkyl, (2–6C)aminoalkyl, (1–4C)alkyl-amino(1–6C)alkyl, (2–8C)dialkylamino(2–6C)alkyl, (1–5C)cyanoalkyl, 3-amino-3-carboxypropyl, 2-(amidinothio)ethyl, 2-(N-aminoamidinothio)ethyl, tetrahydropyran-2-yl, thietan-3-yl, 2-oxopyrrolidinyl, or 2-oxotetrahydro-furan-3-yl, or —R2 is of the formula —(CH$_2$)$_n$—R6 in which n is 1 to 4 and R6 is piperidino, pyrrolidino, morpholino, piperazino or N-methylpiperazino, each value of R6 being optionally substituted by (1–4C)alkyl, phenyl or benzyl, or —R2 is of the formula —(CH$_2$)$_m$—W—R7 in which m is 0 to 3, W is sulphur or a direct bond, and R7 is phenyl or pyridinio(1–4C)alkylene or R7 is pyridyl, imidazolyl, 1,3,4-thiadiazolyl, tetrazolyl, 1-(1–4C)alkyltetrazolyl, thiazolyl, isothiazolyl or isoxazolyl in which the link with W is via a carbon or uncharged nitrogen, each value of R7 being optionally substituted, where possible, by one or two groups selected from (1–4C)alkyl, amino, hydroxy, carboxy, carbamoyl, nitro, (2–5C)alkoxycarbonyl, cyano or sulpho, or —R2 is of the formula —(CH$_2$)$_n$—CO—R8 in which n is 1 to 4 and R8 is (1–4C)alkyl, phenyl or benzyl, or —R2 is of the formula —COR9 or —(CH$_2$)$_n$—OCO—R9 in which n is 1–4 and R9 is hydrogen, (1–4C)alkyl, (1–4C)haloalkyl, phenyl or benzyl, or —R2 is of the formula —G—CH$_2$—R10 in which G is carbonyl or a direct bond and R10 is phthalimido, or —R2 is of the formula —NR11R12R13 in which R11, R12 and R13 are (1–4C)alkyl, or R11 is (1–4C)alkyl and R12 and R13 are joined to form a (3–6C)carbocyclic ring, or R11, R12 and R13 are joined to form a 1-azonia-4-azabicyclo[2,2,2]octane or 1-azonia-3,5,7-triazatricyclo[3,3,1,1$^{3,7}$]decane, or —R2 is of the formula II in which p is 1 or 2 and R14 and R15 are hydrogen or (1–4C)alkyl, or —R2 is of the formula —P(O)R16R17 in which R16 is hydroxy, (1–4C)alkoxy, (2–8C)dialkylamino, phenoxy, phenylamino or one of the values given above for R6, and R17 is (1–4C)alkyl, (1–4C)alkoxy (2–8C)dialkylamino, phenoxy, phenylamino, piperidino, pyrrolidino, morpholino, piperazino or N-methylpiperazino, or —R2 is of the formula —CH$_2$P(O)R18R19 in which R18 and R19 are hydroxy or (1–4C)alkoxy, or —R2 is of the formula —CH(SR20)COOR21 in which R20 is (1–4C)alkyl and R21 is hydrogen or (1–6C)alkyl, or —R2 is of the formula III in which m is 0–3, R22 is hydrogen, (1–3C)alkyl or methylthio, R23 is hydrogen, (1–3C)alkyl, (C$_3$–C$_7$)-cycloalkyl, cyano, carboxy, (2–5C)carboxyalkyl or methanesulphonylamino, or phenyl optionally substituted by amino or hydroxy, or R22 and R23 are joined to form, together with the carbon to which they are attached, a (3–7C) carbocyclic ring, and R24 is hydroxy, amino, (1–4C)alkoxy, (1–4C)alkylamino, phenylamino or of the formula R6 given above or of the formula NHOR25 in which R26 is hydrogen, (1–4C)alkyl, phenyl or benzyl, provided that when R2 contains phenyl, and unless otherwise stated, the phenyl is optionally substituted by 1 or 2 groups selected from halogen, hydroxy, amino, carboxy, nitro, carbamoyl, cyano and aminomethyl;

R3 is hydrogen or methoxy;

R4 is hydrogen, (1–4C)alkyl, halo(1–4C)alkyl, hydroxy(1–4C)alkyl, (1–4C)alkoxy(1–4C)alkyl, carboxy (1–4)alkyl, amino (1–4C)alkyl, cyano(1–4C)alkyl, (1–4C)alkanoylamino(1–4C)alkyl, allyl, furfuryl, benzyl or pyridyl(1–4C)alkyl;

R5 is an aromatic heterocyclic ring system which is linked via carbon and is one of the formula IV to LI inclusive each of these ring systems being optionally substituted where possible, on a carbon atom or atoms, by one, two or three substituents selected from halogen, (1–6C)alkyl, carboxy, (2–6C)alkoxycarbonyl, (2–6C)alkoxycarbonyl(1–4C)alkyl, (1–6C)alkylamino, (2–8C)dialkylamino, benzylamino (optionally substituted in the benzene ring thereof by nitro), thenylamino, allylamino, (1–6C)aminoalkylamino, (1–6C)alkoxy(1–6C)alkylamino, (1–6C)hydroxyalkylamino, hydroxy, mercapto, carbamoyl, (2–6C)alkylcarbamoyl, (3–10C)dialkylcarbamoyl, phenylthio and heteroarylthio wherein heteroaryl is a 5- or 6-membered ring containing 1, 2 or 3 hetero atoms selected from oxygen, nitrogen and sulphur;

and in which Y is oxygen, sulphur or NR27;

Z is nitrogen or CH;

one of A, B, D and E is +NR27 and the remainder are nitrogen;

and ring systems of Formula IV, XVI or XVII, which are optionally fused, on a carbon-carbon bond, with a 5- to 7-membered saturated carbocyclic ring;

R27 is nitrogen-linked and is (1–6C)alkyl, (1–6C)alkyl(2–6C)alkenyl, (2–6C)alkenyl, (2–8C)alkoxyalkyl, carboxy(1–6C)alkyl, [(1–6C)alkoxy]carbonyl(1–6C)alkyl, carbamoyl-(1–6C)alkyl, carboxyamino-carbonyl(1–6C)alkyl, [(1–6C)alkoxy]carbonylamino-carbonyl(1–6C)alkyl, [(2–8C)alkanoyl]methyl, benzoylmethyl, (1–6C)hydroxyalkyl, (1–6C)alkylamino, or phenyl(1–6C)alkyl or phenyl, each optionally substituted by 1 or 2 groups selected from halogen, hydroxy, amino, carboxy, nitro, carbamoyl, cyano, trifluoromethyl, and aminomethyl;

R26 is hydrogen, (1–6C)alkyl, phenyl or benzyl;

R28 is cyano(3–6C)cycloalkenyl, or phenyl optionally substituted by 1 or 2 groups selected from halogen, nitro, amino, (1–4C)alkanoyl, (1–4C)alkanoyl-amino, halo(1–4C)alkyl, hydroxy, carboxy, (2–6C)alkoxy-carbonyl, carbamoyl, mono- or di(1–4C)alkylcarbamoyl, cyano, mesyl, vinyl, and sulpho; or R28 is (2–6C)alkenyl, optionally substituted by halogen, cyano, carbamoyl, mono- or di(1–4C alkyl)carbamoyl, piperidinocarbonyl or morpholinocarbonyl, cyano(1–4C)alkyl, 2-ureidoethyl, 2-thioureidoethyl, 2-(thioacetylamino)ethyl, sulphamoyl, 2-amino-2-carboxyethyl, acetylaminomethyl, phthalimidomethyl, 4,5-dihydroimidazol-2-ylmethyl, 3,4,5,6-tetrahydro-pyrimidin-2-ylmethyl, 2-(1,2,3,6-tetrahydro-2,6-dioxopurin-7-yl)ethyl, 2-hydroxy-iminopropyl (syn or anti) or 2-[(1–4C)alkoxyimino]propyl (syn or anti), or —R28 is of the formula —(CH$_2$)$_2$—NR29R30R31 in which R29, R30 and R31 are (1–4C)alkyl, or —R28 is of the formula —(CH$_2$)$_q$—R32 in which q is 0–2 and —R32 is pyridine, pyridazine, pyrimidine, pyrazine, 1,2,5,6-dihydro-5,6-dioxo-1,2,4-triazine, 2-[(1–4C)alkyl]1,2,5,6-dihydro-5,6-dioxo-1,2,4-triazine, 1-[(1–4C)alkyl]tetrazole, furan, thiophene, pyrrole, 1-[(1–4C)alkyl]pyrrole, oxazole, thiazole, imidazole, 1-[(1–4C)alkyl]imidazole, isoxazole, isothiazole, pyrazole, 1,2,3-thiadiazole, 1-[(1–4C)alkyl]pyrazole, benzfuran, benzthiophene, indole, oxindole, 1-[(1–4C)alkyl]indole, benzoxazole, benzthiazole, benzimidazole, 1-[(1–4C)alkyl]-benzimidazole, 3,4-dihydro-4-oxo-2H-benzo[e]oxazine each of these ring systems being linked to (CH$_2$)$_q$ through carbon and each ring system being optionally substituted by halogen, amino, (1–6C)alkyl, (1–4C)-haloalkyl, (3–6C)-cycloalkyl, (2–6C)alkenyl, carboxy, (2–6C)alkoxycarbonyl, (1–6C)alkoxy, cyano, (2–6C)cyanoalkenyl, carbamoyl, mono- or di (1–4C)alkylcarbamoyl, (1–4C)alkanoylamino, guanidino, hydroxy, nitro, amino; and for those ring systems which contain nitrogen, the N-oxides thereof where chemically possible;

or, when R4 is hydrogen then R5 is also a radical of the formula LI: in which R28 is 2-guanidino-thiazol-4-ylmethyl, hydroxybenzoylmethyl, 2-thenyl, 2-imidazolylmethyl or cinnamyl, optionally substituted by halogen, (1–6C)alkyl, hydroxy, (1–4C)alkoxy, carboxy, (2–6C)alkoxycarbonyl, nitro or carbamoyl, and when R4 is other than hydrogen then R5 is also a radical of the formula LII in which ring J is pyridine, pyrimidine, oxazole, thiazole, isoxazole, isothiazole or imidazole to each of which is optionally fused, when possible, a benzene, cyclopentane or cyclohexane ring; R33 is hydrogen, amino, (1–6C)alkyl, (3–6C)cycloalkyl, (3–6C)alkenyl, (2–8C)alkoxyalkyl, —(CH$_2$)$_r$—COOR35, —(CH$_2$)$_r$—CONH$_2$, —(CH$_2$)$_r$—NH-CO—R36 or —(CH$_2$)$_t$S(O)$_s$—R36 in which t is 1-6, R35 is hydrogen or (1–6C)alkyl, s is 0, 1 or 2, and R36 is (1–6C)alkyl or (1–6C)alkoxy, or R33 is (3–8C)alkanoylmethyl, benzoyl-methyl, (1–6C)primaryhydroxyalkyl, (1–6C)primaryaminoalkyl, (1–4C)alkylamino(1–6C)alkyl, di(1–4C)-alkylamino(1–6C)alkyl, carbamoyl(1–4C)alkyl, mono- or di(1–4C)alkylcarbamoyl(1–4C)alkyl, (1–4C)alkoxy-(1–4C)alkyl, (1–6C)alkoxy, (1–4C)alkoxy(2–4C)alkoxy(1–4C)alkyl, (1–6C)alkylamino, phenyl(1–6C)-alkyl or phenyl(1–6C)alkoxy or of the formula (CH$_2$)$_2$N= R37NR38R39 or (CH$_2$)$_n$C(NR37)NR38R39 or a tautomer thereof in which R37, R38 and R39 are hydrogen or (1–4C)alkyl;

R34 is hydrogen or one or two substituents selected from halogen, amino, nitro, (1–6C)alkyl, carboxy, (2–6C)alkoxycarbonyl, (1–6C)alkoxy, cyano, carbamoyl, (1–6C)haloalkyl, (1–6C)azidoalkyl, (1–6C)aminoalkyl, (2–4C)aminoalkylthio(1–4C)alkyl, (2–6C)alkanoylamino, (2–4C)alkanoylamino(1–4C)alkyl, (2–6C)alkanoyloxy(1–4C)alkyl, benzyl, benzyloxy and heteroarylthio, wherein, when R33 contains phenyl, the phenyl is optionally substituted by halogen, nitro, (1–6C)alkyl, hydroxy, (1–4C)alkoxy, carboxy, (2–6C)alkoxycarbonyl, carbamoyl, sulphamoyl, sulpho, mono- or di(1–4C)alkylcarbamoyl, or mono- or di-(1–4C)alkylsulphamoyl, and wherein when R34 is heteroarylthio, the heteroaryl ring is a 5- or 6-membered ring containing 1,2 or 3 hetero atoms selected from oxygen, nitrogen and sulphur;

and the salts formed with acids and bases which afford pharmaceutically acceptable anions and cations respectively.

It is to be understood that in the above formula I and throughout this specification, the illustrated stereochemistry of the ceph-3-em nucleus, and its optional modifications at the 1-position, is the absolute configuration. It is also to be understood that, since R5 contains a quaternary nitrogen, the compounds of the formula I will normally exist in zwitter-ionic form, involving the quaternary nitrogen and the carboxy group. When the compound of the formula I contains further acidic or basic substituents, it is to be understood that the possibility of a double zwitter-ionic form of the compound will arise. Alternatively, exogenous anions or cations may be included, to form pharmaceutically-acceptable base-addition or acid-addition salts, as defined above.

We have now discovered that in the preparation of compounds of formula I wherein R$^4$ is a (1–4C)alkyl group, particularly where R$^4$ is an ethyl group, it may be advantageous to proceed via certain novel intermediate compounds which may be isolated in the course of the preparation.

Accordingly the invention provides a compound of the formula LIII wherein X is sulphur, oxygen, methylene or sulphinyl (R or S configuration), R$^3$ is hydrogen or methoxy, R$^{54}$ is hydrogen or a carboxyl protecting group and R$^{51}$ is a (1–4C)alkyl group, particularly an ethyl group, and acid-addition and base-addition salts thereof.

Preferred compounds of formula I are those wherein X is sulphur and R3 and R54 are both hydrogen. A particularly preferred compound of formula LIII is thus the compound 7-amino-3-ethylaminomethylceph-3-em-4-carboxylic acid.

We have further found that it may be advantageous as a further step in the preparation of compounds of formula I to employ an intermediate compound wherein the substituted amino group at the C3' position is protected by a suitable protecting group. Such protected compounds are also novel.

Accordingly the invention further provides compounds of formula LIV wherein X, R$^3$ and R$^{54}$ are as hereinbefore defined; R$^4$ is hydrogen, (1–4C)alkyl, halo(1–4C)alkyl, hydroxy(1–4C)alkyl, (1–4C)alkoxy(1–4C)alkyl, carboxy (1–4C)alkyl, amino (1–4C)alkyl, cyano(1–4C)alkyl, (1–4C)alkanoylamino(1–4C)alkyl, allyl, furfuryl, benzyl or pyridyl(1–4C)alkyl and R$^{52}$ is an amino protecting group, and acid addition and base-addition salts thereof.

When reference is made to protecting groups being present at any position in the compounds described herein such protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1-4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

Examples of carboxyl protecting groups include straight or branched chain (1–12C)alkyl groups (e.g. isopropyl, t-butyl); halo lower alkyl groups (e.g. 2-iodoethyl, 2,2,2-trichloroethyl); lower alkoxy lower alkyl groups (e.g. methoxymethyl, ethoxymethyl, isobutoxymethyl); lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); and (2–6C)alkenyl groups (e.g. vinylethyl).

Methods particularly appropriate for the removal of carboxyl protecting groups include for example acid-, base- or ezymically-catalysed hydrolysis.

Examples of amino protecting groups include aryl lower alkyl groups (e.g. benzyl and substituted benzyl, e.g. p-methoxybenzyl and 2,4-dimethoxybenzyl, and triphenylmethyl); di-p-anisylmethyl and furylmethyl groups; acyl (e.g. lower alkoxycarbonyl and aryl lower alkoxycarbonyl e.g. t-butoxycarbonyl and benzyloxycarbonyl); tri lower alkylsilyl (e.g. trimethylsilyl and t-butyldimethylsilyl); lower alkylidene (e.g. methylidene); benzylidene and substituted benzylidene groups; and the phthalimido group.

Particular compounds of formula LIV are those wherein $R^4$ is a (1–4C) alkyl group especially an ethyl group.

Particularly preferred compounds of formula LIV are the C3'-amino protected forms of 7-amino-3-ethylaminomethylceph-3-em-4-carboxylic acid.

Although the compounds of formula LIII and LIV are, as hereinbefore stated, particularly appropriate intermediates for use in the preparation of the compounds of formula I, as disclosed in European Patent Application 85303662.2, their utility extends to the preparation of any related compounds having a 7-acylamido group and an appropriate N-substituted 3-aminomethyl group. The use of the compounds of formulae LIII and LIV in the preparation of such compounds constitutes a further feature of the invention, as do the said compounds whenever prepared by such processes.

The desired group $R^5$ in the compounds of formula I may be introduced for example by reaction of a compound of formula LIII with a compound of formula $R^5-R^{40}$, where $R^{40}$ is a displaceable radical.

The desired 7-position acylamido group may be introduced by known methods, for example, where a compound of formula I is required, reaction with an acid of formula LV (in which $R^1$ and $R^2$ are as hereinbefore defined) or a reactive derivative thereof.

A particular method for the preparation of compounds of formula I is to carry out the introduction of the 7-position group on a compound of formula LIV followed by deprotection of the 3-aminomethyl group and introduction of the group $R^5$.

The compounds of the formula LIII may be prepared for example by deprotection of the 7-amino group of a compound of formula LVI wherein X, $R^3$, $R^{51}$ and $R^{54}$ are as hereinbefore defined and $R^{53}$ represents an amino protecting group, for example one of those listed above, particularly a t-butoxycarbonyl group. The said process accordingly forms a further feature of the invention.

Compounds of formula LVI may be prepared for example by reaction of a compound of formula LVII with the appropriate aldehyde in the presence of a reducing agent (e.g. sodium cyanoborohydride). For example, where $R^{51}$ represents ethyl, the appropriate aldehyde is acetaldehyde.

Compounds of formula LIV may be prepared for example by reaction of a compound of formula LIII or a corresponding compound having a group $R^4$ which is other than a (1–4C) alkyl group in place of the group $R^{51}$ (which compounds may be prepared by analogous methods to those just described for compounds of the formula LIII) with a reagent capable of introducing the required amino protecting group $R^{52}$. Such reagents are well known and described in the literature. For example, where $R^{52}$ is a t-butoxycarbonyl group a suitable reagent is the anhydride of the formula $(tBuOCO)_2O$ or the corresponding acid chloride tBuOCOCl. Such processes for the preparation of compounds of formula LIV accordingly form further features of the invention.

Salts of the compounds of formula LIII and LIV may be prepared by reaction of the compound of formula LIII or LIV with an appropriate acid or base.

The following Examples are provided to illustrate the invention, but do not imply any limitation of the scope thereof.

Nmr spectra are quoted in delta relative to tetramethylsilane (delta=0) as internal standard (s=singlet, d=doublet, t=triplet, q=quartet, m=multiplet, br=broad); field strength 90 MHz; J=coupling constant.

EXAMPLE 1

7-amino-3-ethylaminomethylceph-3-em-4-carboxylic acid (trifluoroacetic acid salt)

7-t-butoxycarbonylamino-3-ethylaminomethyl-ceph-3-em-4-carboxylic acid (66 mg) was stirred with 3 cm$^3$ of trifluoroacetic acid for two hours, the reaction being monitored by high pressure liquid chromatography (HPLC). The reaction mixture was evaporated, dried under vacuum, and the residue triturated with ether to give a solid (71 mg); nmr in DMSOd$_6$/CD$_3$COOD: 1.20 (t,3H); 2.85–3.06 (m,2H); 3.66 (s, 2H); 3.74 (d,1H); 3.92 (d,1H); 5.05 (d,1H); 5.10 (d,1H).

The starting material 7-t-butoxycarbonylamino-3-ethylaminomethylceph-3-em-4-carboxylic acid was prepared as follows:

3-Aminomethyl-7-(t-butoxycarbonylaminoceph-3-em-4-carboxylic acid (987 mg at approximately 71% purity, equivalent to 700 mgs pure material) was added to a rapidly stirred solution of Et$_3$N (215 mg, 0.294 ml) at ambient temperature: it did not dissolve completely. The mixture was stirred for 30 minutes, then NaCNBH$_3$ (132 mg) was added, followed by acetaldehyde (0.119 ml, 93.7 mg) as a solution in methanol, over 40 minutes by infusion pump. The mixture was stirred for 1 hour at ambient temperature after which HPLC showed much starting material still remaining. A further 0.018 ml of acetaldehyde was added in one portion over about 20 seconds. HPLC after a further 30 minutes showed less starting material present. The mixture was evaporated to a foam, then dissolved in 50 ml water adjusted to pH 2–3 with acetic acid, and purified by medium pressure chromatography on HP-20 ss column using gradient elution with water up to 25% v/v acetonitrile. The product eluted at 13–15% acetonitrile.

Acetonitrile was removed by evaporation and the product freeze dried to give 310 mgs, contaminated with some starting material. Nmr in DMSOd$_6$/CD$_3$COOD 1.39 (s,9H); 1.19 (t,3H); 2.95 (q,2H); 3.36 (d,1H); 3.77 (d, 1H); 3.43 (d,1H); 3.56 (d,1H); 4.90 (d,1H); 5.39 (br.d,1H).

EXAMPLE 2

7-amino-3-N-t-butoxycarbonyl-N-ethylaminomethyl-ceph-3-em-4-carboxylic acid

Method A 1.82 g of 7-amino-3-ethylaminomethylceph-3-em-4-carboxylic acid (e.g. prepared as in Example 1 above) was dissolved in water (20 ml) and NaHCO$_3$ (1.7 g) in water (10 ml) was added. (tBuOCO)$_2$O (1.85 g) in solution in dioxan (20 ml) was added and the mixture stirred at room temperature overnight. The reaction was observed to be incomplete (by HPLC). A second portion of (tBuOCO)$_2$O (500 mg) was added and the reaction continued for 4 hours. The mixture was diluted with water and washed with ether (X2). The aqueous phase was cooled to 0° C. and the pH adjusted to 4.5 with acetic acid. The product precipitated as a white powder (1 g: yield 40%); nmr in DMSOd$_6$/TFAd/CD$_3$COOD: 1.03 (t,3H); 1.42 (s,9H); 3.18 (q,2H); 3.47 (s,2H); 4.2 and 4.4 (2d, 2H J=16.8 Hz); 5.14 (d,1H, J=4.8 Hz); 5.20 (d,1H, J=4.8 Hz).

Method B

To a slurry of 7-amino-3-ethylaminomethylceph-3-em-4-carboxylic acid p-toluene sulphonic acid salt (which may be prepared for example by the method of Example 3(a) below) (43.19 g at 47.6% strength=0.08 mole as zwitterion) in dichloromethane (240 ml) held at 20° C. with a water bath was added triethylamine (33.39 ml), 0.24 mole) over 5 minutes. A solution of (tBuO-CO)$_2$O (34.88 g, 0.16 mole) in dichloromethane (160 ml) was then added, also over 5 minutes. The reaction was monitored by HPLC. After 25 minutes it was complete. Water (300 ml) was added and after 20 min stirring the layers were settled and separated. The organic phase was washed with water (100 ml) and the aqueous phases were combined, cooled to 0° C. and adjuste slowly to pH 4.5 with glacial acetic acid (ca. 12 ml). After stirring at 0° C. for 1 h the amorphous solid was filtered off, displacement washed with ether (240 ml) slurried with ether (240 ml) and sucked dry for 5 minutes before drying over P$_2$O$_5$ in a vacuum desiccator, to yield 30.74 g of the desired product.

EXAMPLE 3

(a)

7-Amino-3-ethylaminomethylceph-3-em-4-carboxylic acid (p-toluenesulphonic acid salt)

7-Amino-3-ethylaminomethylceph-3-em-4-carboxylic acid (5 g., 70% strength) was dissolved in water (5 ml) and p-toluene-sulphonic acid monohydrate (2.59 g) added at room temperature. Iso-propanol (20 ml) was slowly added with stirring and the mixture cooled to 0° C. After 2 hours, the deposited crystalline title salt (2.9 g) was collected by filtration and thoroughly washed with ice-cold isopropanol.

(b)

7-Amino-3-ethylaminomethylceph-3-em-4-carboxylic acid (naphthalene-2-sulphonic acid salt)

Example 3(a) was repeated using 0.1 g of 7-amino-3-ethylaminomethylceph-3-em-4-carboxylic acid and naphthalene-2-sulphonic acid (1 equivalent) to give 0.07 g. of the title salt.

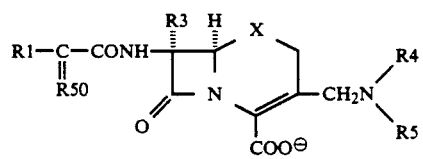

$$-(CH_2)_p-\underset{\underset{R15}{R14}}{C}-COOH \qquad \text{II}$$

$$-\underset{\underset{R23}{|}}{\overset{\overset{R22}{|}}{C}}-(CH_2)_m-COR24 \qquad \text{III}$$

IV

V

VI

VII

-continued
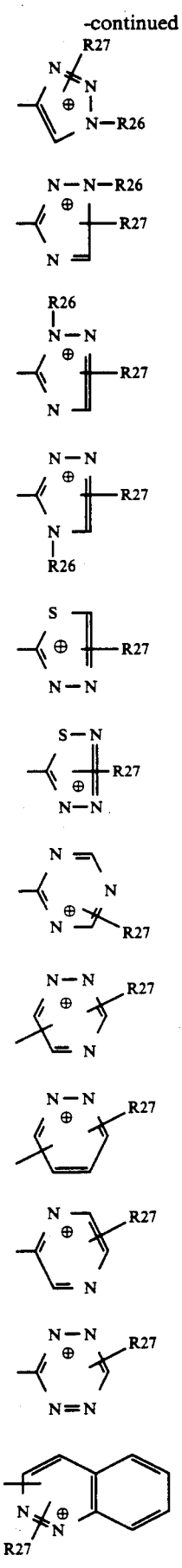
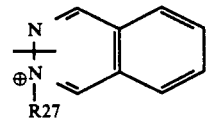 VIII
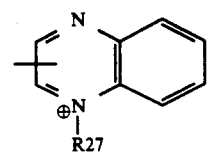 IX
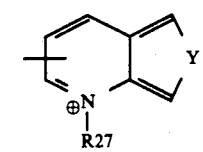 X
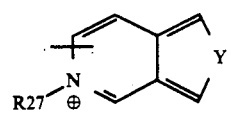 XI
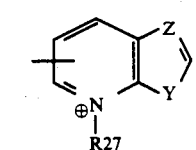 XII
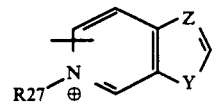 XIII
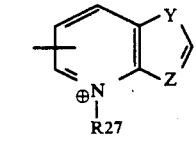 XIV
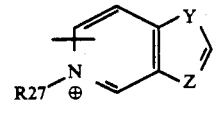 XV
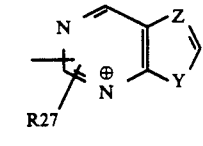 XVI
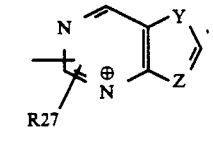 XVII
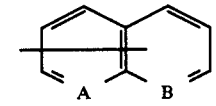 XVIII

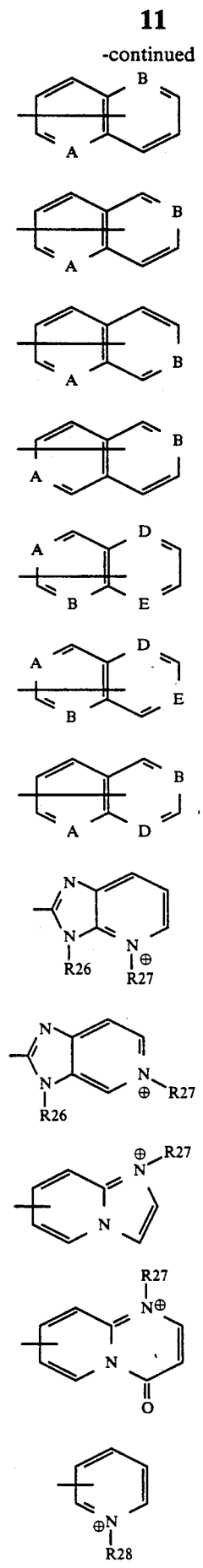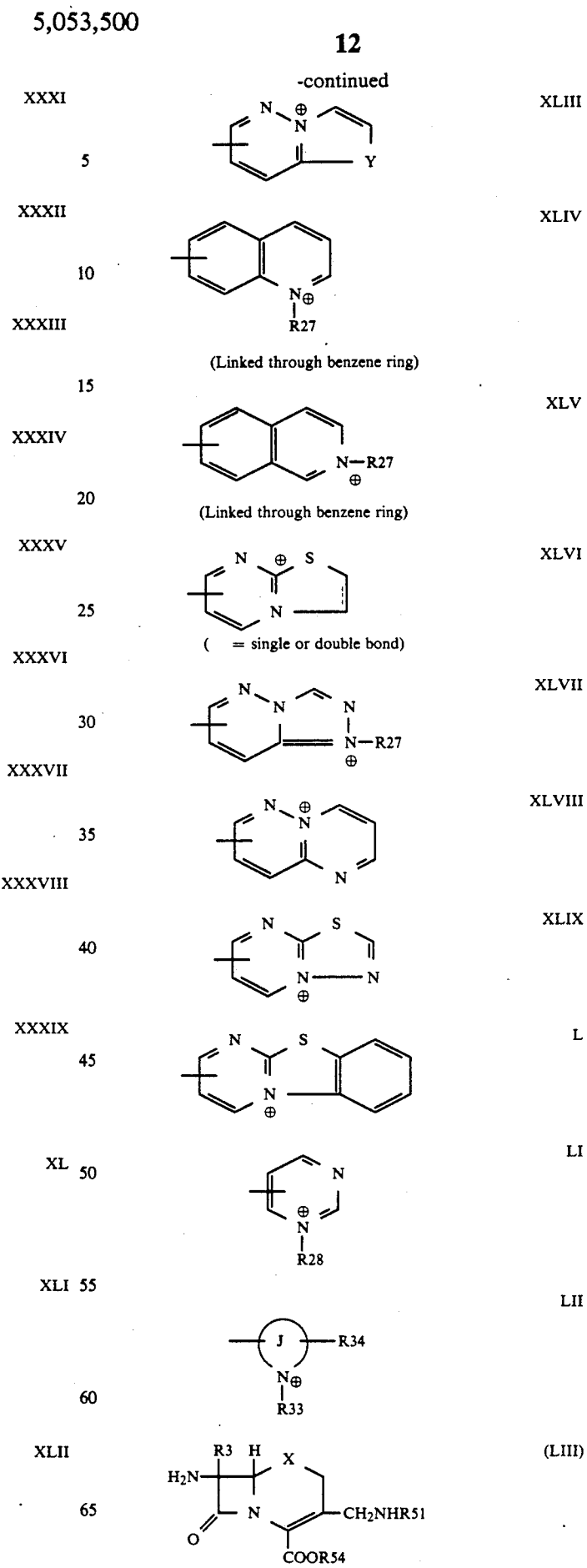

-continued

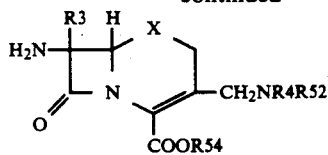

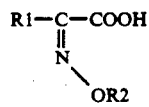

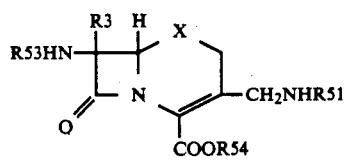

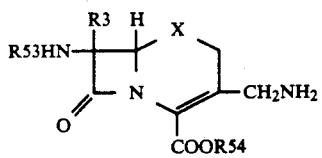

We claim:
1. A compound of the formula LIV

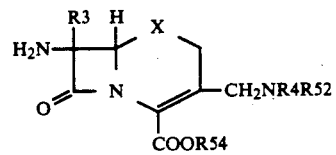

wherein X is sulphur or sulphinyl (R or S configuration), $R^3$ is hydrogen or methoxy, $R^{54}$ is hydrogen or a carboxyl protecting group and $R^4$ is hydrogen, (1-4C)alkyl, halo(1-4C)alkyl, hydroxy(1-4C)alkyl, (1-4C)alkoxy(1-4C)alkyl, carboxy(1-4)alkyl, amino(1-4C)alkyl, cyano(1-4C)alkyl, (1-4C)alkanoylamino(1-4C)alkyl, allyl, furfuryl, benzyl or pyridyl(1-4C)alkyl; and $R^{52}$ is aryl$C_{1-4}$alkyl, di-p-anisylmethyl, furylmethyl, aryl$C_{1-4}$alkoxycarbonyl, tri$C_{1-4}$alkylsilyl, $C_{1-4}$alkylidene, benzylidene, substituted benzylidene and phthalimido, and acid-addition and base-addition salts thereof.

2. The compound of formula LIV as claimed in claim 1 wherein $R^4$ is an ethyl group.

3. The compound of formula LIV as claimed in claim 1 wherein R52 is a aryl$C_{1-4}$alkoxycarbonyl group.

4. 7-amino-3-N-t-butoxycarbonylaminomethylceph-3-em-4-carboxylic acid.

5. The compound as claimed in claim 1 wherein $R^4$ is a (1-4C) alkyl group.

* * * * *